US010658072B2

(12) United States Patent
Karlsson

(10) Patent No.: US 10,658,072 B2
(45) Date of Patent: May 19, 2020

(54) METHOD AND SYSTEM FOR INTERACTION ANALYSIS

(71) Applicant: GE Healthcare Bio-Sciences AB, Uppsala (SE)

(72) Inventor: Robert Karlsson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 464 days.

(21) Appl. No.: 15/428,342

(22) Filed: Feb. 9, 2017

(65) Prior Publication Data

US 2018/0224439 A1 Aug. 9, 2018

(51) Int. Cl.
*G16B 45/00* (2019.01)
*G01N 33/543* (2006.01)
*G01N 33/557* (2006.01)
*G16B 40/00* (2019.01)
*G16B 20/00* (2019.01)

(52) U.S. Cl.
CPC ....... *G16B 45/00* (2019.02); *G01N 33/54373* (2013.01); *G01N 33/557* (2013.01); *G16B 20/00* (2019.02); *G16B 40/00* (2019.02)

(58) Field of Classification Search
None
See application file for complete search history.

(56) References Cited

U.S. PATENT DOCUMENTS

2014/0185051 A1* 7/2014 Guan ............... G01N 21/553
356/445
2017/0038379 A1* 2/2017 Karlsson .......... G01N 33/54373

FOREIGN PATENT DOCUMENTS

WO    WO 2015/114056    *  6/2015   ........... G01N 33/543

OTHER PUBLICATIONS

Robert Karlsson, "Comparison of surface plasmon resonance binding curves for characterization of protein interactions and analysis of screening data", Analytical Biochemistry, 502, 2006, pp. 53-63.

* cited by examiner

*Primary Examiner* — Melanie Brown
*Assistant Examiner* — Richard Moerschell
(74) *Attorney, Agent, or Firm* — Eversheds Sutherland (US) LLP

(57) ABSTRACT

The present invention relates to a method of evaluation of molecular binding interactions at a sensing surface, and more particularly to a method for evaluation of screening data obtained from an interaction between an analyte in a fluid sample and a ligand immobilized on a sensor surface of a biosensor that is independent of interaction models. Preferably the biosensor is a SPR biosensor.
The invention also relates to a biosensor system arranged to perform the method and a computer program arranged to control the operation of the biosensor system.

19 Claims, 6 Drawing Sheets

Reference windows

Reference binding window 1
Stable binding

Reference binding window 2
Less stable binding

Sample assignments

Upper and lower limits dashed lines
Two samples –solid lines - assigned to stable binding reference window Upper and lower limits dashed lines
Samples - solid lines -assigned to less stable binding

METHOD AND SYSTEM FOR INTERACTION ANALYSIS

FIELD OF THE INVENTION

The present invention relates to a method of evaluation of molecular binding interactions at a sensing surface, and more particularly to a method for evaluation of screening data obtained from an interaction between an analyte in a fluid sample and a ligand immobilized on a sensor surface of a biosensor that is independent of interaction models.

BACKGROUND OF THE INVENTION

Analytical sensor systems that can monitor interactions between molecules, such as biomolecules, in real time are gaining increasing interest. These systems are often based on optical biosensors and usually referred to as interaction analysis sensors or biospecific interaction analysis sensors. A representative such biosensor system is the BIACORE® instrumentation sold by GE Healthcare, which uses surface plasmon resonance (SPR) for detecting interactions between molecules in a sample and molecular structures immobilized on a sensing surface. As sample is passed over the sensor surface, the progress of binding directly reflects the rate at which the interaction occurs. Injection of sample is followed by a buffer flow during which the detector response reflects the rate of dissociation of the complex on the surface. A typical output from the BIACORE® system is a graph or curve describing the progress of the molecular interaction with time, including an association phase part and a dissociation phase part. This binding curve, which is usually displayed on a computer screen, is often referred to as a binding curve or "sensorgram".

With the BIACORE® system (and analogous sensor systems) it is thus possible to determine in real time without the use of labeling, and often without purification of the substances involved, not only the presence and concentration of a particular molecule (analyte) in a sample, but also additional interaction parameters, including kinetic rate constants for binding (association) and dissociation in the molecular interaction as well as the affinity for the surface interaction. The association rate constant ($k_a$) and the dissociation rate constant ($k_d$) can be obtained by fitting the resulting kinetic data for a number of different sample analyte concentrations to mathematical descriptions of interaction models in the form of differential equations. The affinity (expressed as the affinity constant $K_A$ or the dissociation constant $K_D$) can be calculated from the association and dissociation rate constants.

In order to derive the above interaction parameters from registered binding curves there has been developed a range of different assays and models involving more or less complex calculations which have proven to give very reliable results for many types of interactions. However, many of these calculations are based on a specific interaction model and thus are limited to interactions of a specific type that fall under this model and there are a range of interactions that are not easily categorized according to a specific model. Therefore, it is not always possible to provide reliable interaction parameters for evaluation of some analyte ligand interactions.

One alternative method to evaluate this type of interactions is to rely on report points at predetermined points in the binding curve. But in analysis based on report points, only information about the interaction at the specific time points is used to characterize the interaction, whereas a majority of the information in the binding curves is discarded.

SUMMARY OF THE INVENTION

The object of the invention is to provide a novel method and biosensor system for evaluation of an interaction between an analyte in a fluid sample and a ligand immobilized on a sensor surface of a biosensor, which method and biosensor system overcomes one or more drawbacks of the prior art. This is achieved by the method and biosensor system as defined in the independent claims.

In a first aspect the invention relates to a method for screening a sample in respect of the presence of at least one specific analyte possibly present in a fluid sample by evaluating data from interaction between the specific analyte, if present, and its ligand or binding partner, which comprises the steps of:
 a) providing a sensor surface comprising at least one immobilized ligand, wherein each ligand is known to bind and interact with a specific analyte;
 b) obtaining a plurality of different reference binding curves, each representing a specific binding behavior between a specific analyte and its ligand, or binding partner known to interact with the specific analyte, for a predetermined acquisition cycle;
 c) acquiring, using the biosensor, a sample binding curve for interaction between the specific analyte possibly present in the fluid sample and its ligand or binding partner for the same predetermined acquisition cycle;
 d) registering the deviation of the sample binding curve from the reference binding curves to form reference interaction window;
 e) assigning the interaction between specific analyte and its ligand or binding partner from step c) to the reference interaction window to which it shows the smallest registered deviation;
 and f) optionally repeating steps c)-e) with additional fluid samples.

For example the method may be repeated 10-10000 times. In one embodiment the steps are repeated 384 times or cycles, one cycle for each sample present in a 384 well plate. If the sample library contains ten filled 384 well plates then 3840 cycles will be run. The method of the invention is not limited to any number of cycles.

Preferably 1-1000 ligands are immobilized as discrete areas or spots on said sensor surface. Thus, up to 1000 analytes can be screened for simultaneously in one sample in one cycle and one sample may generate up to 1000 sample binding curves. A desired range would be 2 to 400, such as 2, 8, 96 or 384 but there is no limitation set by the method.

In further aspects, the invention relates to a biosensor system and a computer program.

One advantage with the method and biosensor system of the present invention is that it allows evaluation of analyte ligand/binding partner interactions that is independent of theoretical interaction models, while still taking all registered data points into account. Another advantage is that the evaluation is less complex compared to prior art evaluation methods, and therefore requires less computational power.

A more complete understanding of the present invention, as well as further features and advantages thereof, will be obtained by reference to the following detailed description and drawings.

DETAILED DESCRIPTION OF THE INVENTION

Figure 1:
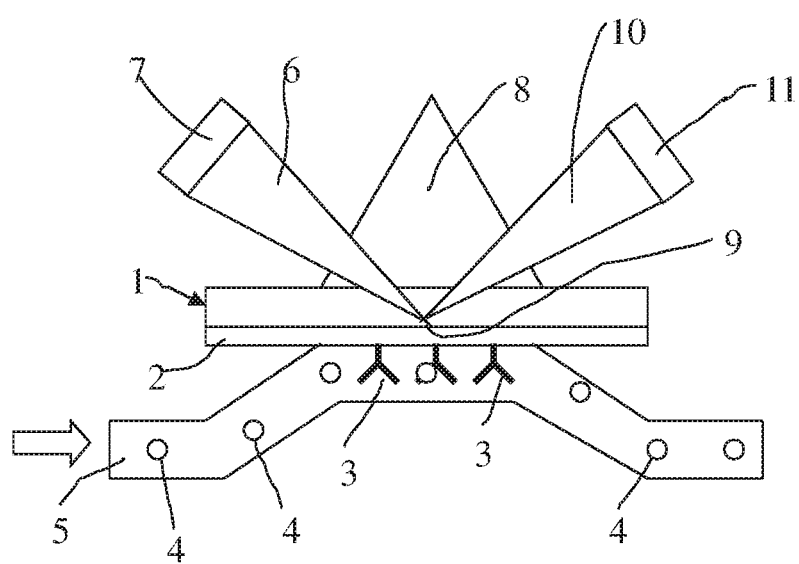
FIG. 1 is a schematic side view of a biosensor system based on SPR (prior art).

As mentioned above, the present invention relates to a method for evaluation of screening data obtained from an interaction between an analyte in a fluid sample and a ligand immobilized on a sensor surface of a biosensor that is independent of interaction models and provides more information than report point analysis.

Typically, the experimental binding data is obtained by sensor-based technology, which studies the molecular interactions and presents the results in real time as the interactions progress. Before describing the present invention in more detail, however, the general context in which the invention is intended to be used will be described.

Chemical sensors or biosensors are typically based on label-free techniques, detecting a change in a property of a sensor surface, such as e.g. mass, refractive index, or thickness for the immobilised layer, but there are also sensors relying on some kind of labelling. Typical sensor detection techniques include, but are not limited to, mass detection methods, such as optical, thermo-optical and piezoelectric or acoustic wave methods (including e.g. surface acoustic wave (SAW) and quartz crystal microbalance (QCM) methods), and electrochemical methods, such as potentiometric, conductometric, amperometric and capacitance/impedance methods. With regard to optical detection methods, representative methods include those that detect mass surface concentration, such as reflection-optical methods, including both external and internal reflection methods, which are angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) (which may include scatter enhancing labels), optical wave guide sensors; external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers (e.g. Bio-Layer Interferometry as implemented by ForteBio®), waveguide leaky mode spectroscopy, reflective interference spectroscopy (RIfS), transmission interferometry, holographic spectroscopy, and atomic force microscopy (AFR).

While in the detailed description and Examples that follow, the present invention is illustrated in the context of SPR spectroscopy, and more particularly the BIACORE® system, it is to be understood that the present invention is not limited to this detection method. Rather, any affinity-based detection method where an analyte binds to a ligand immobilised on a sensing surface may be employed, provided that a change at the sensing surface can be measured which is quantitatively indicative of binding of the analyte to the immobilised ligand thereon.

A schematic illustration of the BIACORE® system is shown in FIG. 1. Sensor chip 1 has a gold film 2 supporting capturing molecules (ligands) 3, e.g. antibodies, exposed to a sample flow with analytes 4, e.g. an antigen, through a flow channel 5. Monochromatic p-polarised light 6 from a light source 7 (LED) is coupled by a prism 8 to the glass/metal interface 9 where the light is totally reflected. The intensity of the reflected light beam 10 is detected by an optical detection unit 11 (photodetector array).

When molecules in the sample bind to the capturing molecules on the sensor chip surface, the concentration, and therefore the refractive index at the surface changes and an SPR response is detected. Plotting the response against time during the course of an interaction will provide a quantitative measure of the progress of the interaction. Such a plot, or kinetic or curve (binding isotherm), is usually called binding curve or sensorgram, also sometimes referred to in the art as "affinity trace" or "affinogram". In the BIACORE® system, the SPR response values are expressed in resonance units (RU). One RU represents a change of 0.0001° in the angle of minimum reflected light intensity, which for most proteins and other biomolecules correspond to a change in concentration of about 1 $pg/mm^2$ on the sensor surface. As sample containing an analyte contacts the sensor surface, the capturing molecule (ligand) bound to the sensor surface interacts with the analyte in a step referred to as "association." This step is indicated in the binding curve by an increase in RU as the sample is initially brought into contact with the sensor surface. Conversely, "dissociation" normally occurs when the sample flow is replaced by, for example, a buffer flow. This step is indicated in the binding curve by a drop in RU over time as analyte dissociates from the surface-bound ligand.

Figure 2:
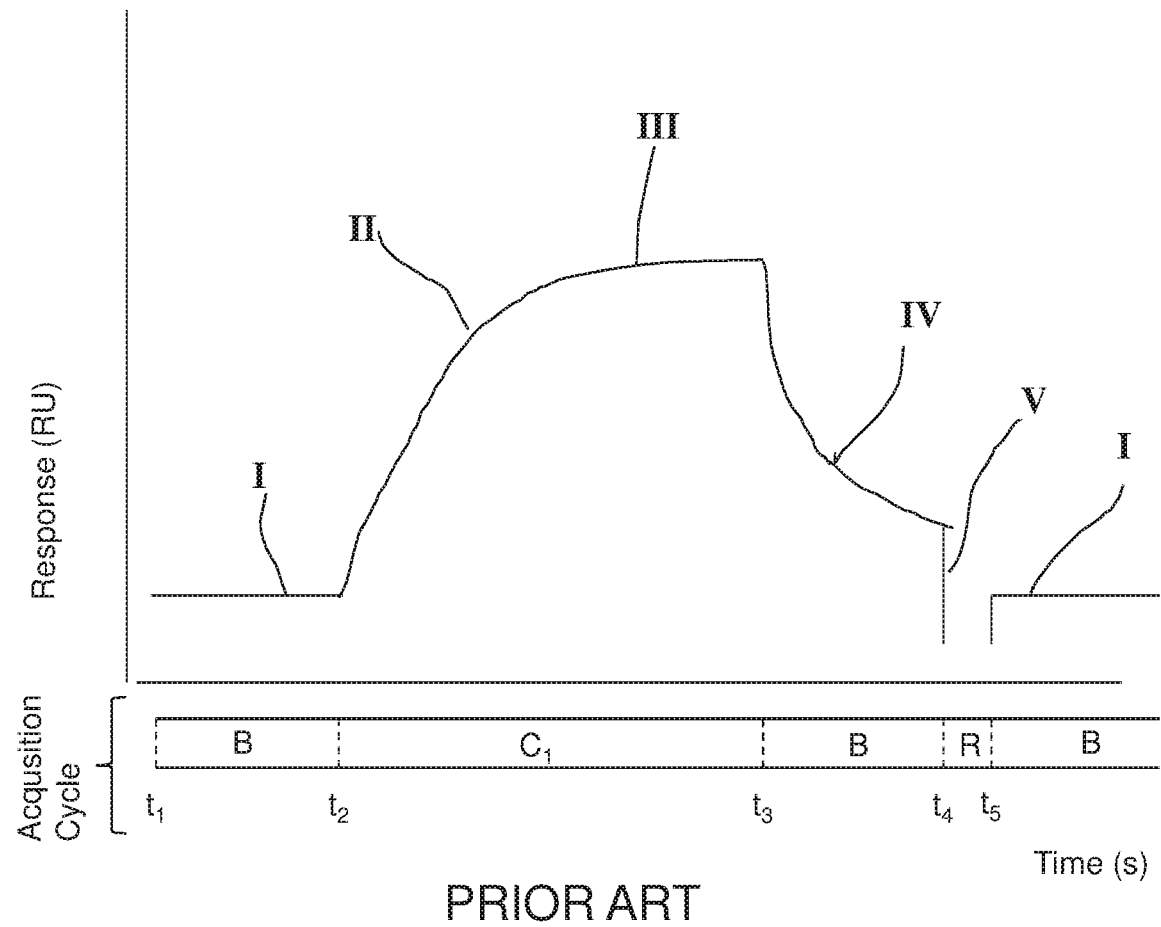
FIG. 2 is a representative sensorgram where the binding curve has visible association and dissociation phases (prior art).

A representative binding curve (sensorgram) for a reversible interaction at the sensor chip surface is presented in FIG. 2, the sensing surface having an immobilised capturing molecule, or ligand, for example an antibody, interacting with a binding partner therefore, or analyte, in a sample. The binding curves produced by biosensor systems based on other detection principles mentioned above will have a similar appearance. The vertical axis (y-axis) indicates the response (here in resonance units, RU) and the horizontal axis (x-axis) indicates the time (here in seconds). Below the horizontal axis, the acquisition cycle for acquiring a binding curve is schematically disclosed divided in different time sections where the sensor surface is put into contact with different fluids. Initially, from $t_1$ to $t_2$, buffer (B) is passed over the sensing surface giving the baseline response I in the binding curve. Then, during from $t_2$ to $t_3$, the sensor surface is contacted with a sample containing an analyte at a concentration $C_1$ whereby an increase in signal is observed due to binding of the analyte. This part II of the binding curve is usually referred to as the "association phase". Eventually, a steady state condition is reached at or near the end of the association phase where the resonance signal plateaus at III (this state may, however, not always be achieved). It is to be noted that herein the term "steady state" is used synonymously with the term "equilibrium" (in other contexts the term "equilibrium" may be reserved to describe the ideal interaction model, since in practice binding could be constant over time even if a system is not in equilibrium). At the end of the association phase, at $t_3$, the sample is often replaced with a continuous flow of buffer (B) and a decrease in signal reflects the dissociation, or release, of analyte from the surface. This part IV of the binding curve is usually referred to as the "dissociation phase". The analysis is optionally ended by a regeneration step, at $t_4$, where a solution capable of removing bound analyte from the surface (R), while (ideally) maintaining the activity of the ligand, is injected over the sensor surface. This is indicated in part V of the sensorgram. At $t_5$ injection of buffer (B) restores the baseline I and the surface is now ready for a new analysis. In some situations, it may be convenient to omit the regeneration step V and initiate a new injection cycle without regeneration. Examples of such situations comprise concentration series of the same analyte, screening of analytes with a sufficiently high dissociation rate to allow essentially complete dissociation, etc.

From the profiles of the association and dissociation phases II and IV, respectively, information regarding the binding and dissociation kinetics is obtained, and the height of the binding curve at III represents affinity (the response resulting from an interaction being related to the change in mass concentration on the surface).

As mentioned above, the present invention relates to a method for evaluation of screening data obtained from an interaction between an analyte in a fluid sample and a ligand immobilized on a sensor surface of a biosensor that is independent of interaction models and provides more information than report point analysis.

Figure 3:
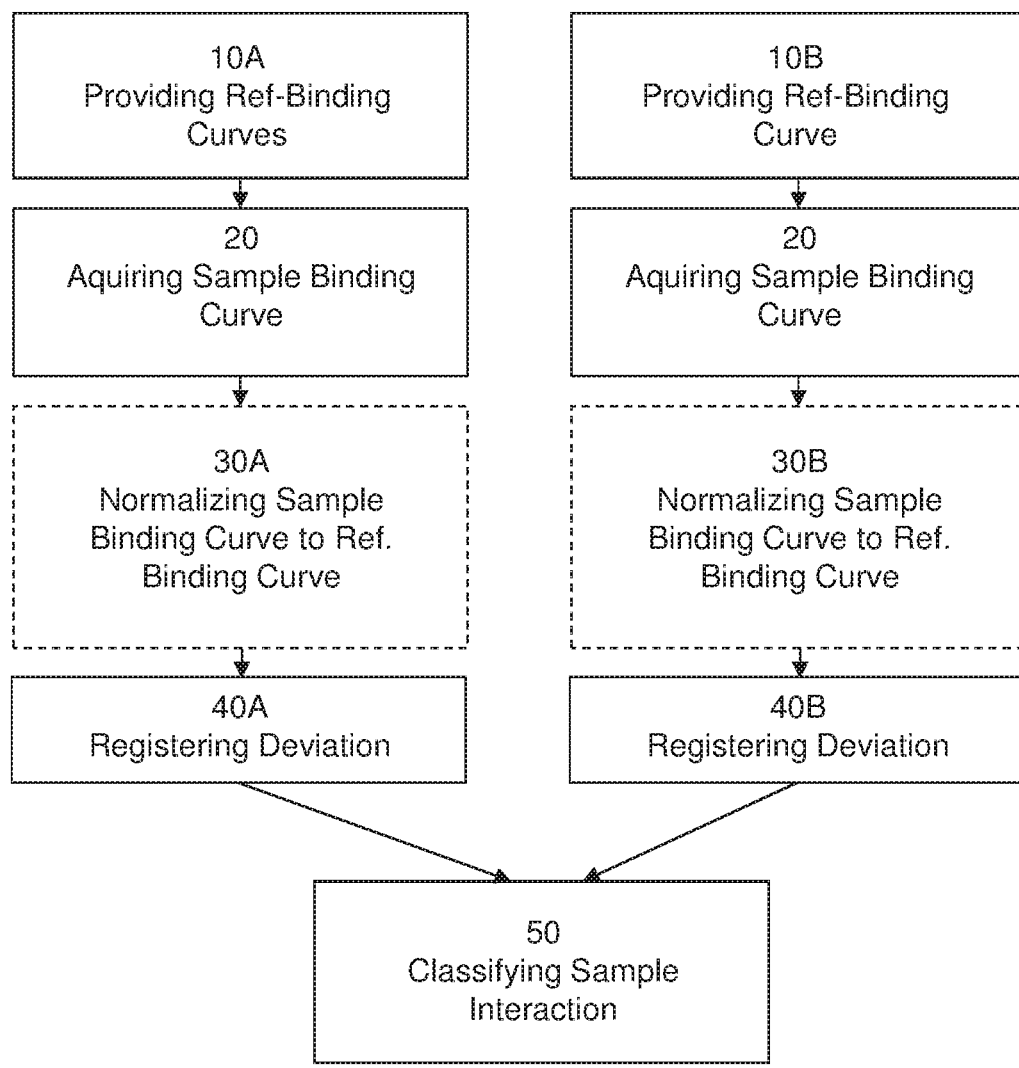
FIG. 3 shows a schematic block diagram of a method according to one embodiment of the present invention.

The biosensor may be based on any type of affinity-based detection method where an analyte binds to a ligand immobilised on a sensing surface, provided that a change at the sensing surface can be measured which is quantitatively indicative of binding of the analyte to the immobilised ligand thereon. According to one embodiment, schematically disclosed in FIG. 3, the method comprises the assignment of a sample curve to one of at least two reference windows where each window is obtained by
- providing upper and lower reference binding curves 10A and 10B, representing a number of reference windows for predetermined acquisition cycles,
- acquiring, using the biosensor, a sample binding curve 20 for the analyte ligand interaction for the predetermined acquisition cycle,
- registering the deviation of the sample binding curve from the reference binding curves to form reference interaction windows 40A and 40B, and
- assigning or classifying the sample interaction 50 of the analyte to the reference interaction window for which the smallest deviation is obtained As indicated by the dashed box in FIG. 3, the method may optionally comprise the step of normalizing 30A, 30B the binding curves 10 and 20 before the deviation is registered. Such normalization may be used to compensate for variations in ligand activity on the sensor surface.

Throughout this disclosure, the term reference binding curve refers to a binding curve that is characteristic for a reference interaction such as:
- an interaction between a specific analyte-ligand pair,
- a particular interaction type that may be common to a group of two or more analyte-ligand pairs,
- a particular interaction behaviour indicative of a specific interaction mechanism, The reference binding curve may be provided in essentially any suitable way, and it may be a direct binding curve for a particular interaction that is used directly as acquired using a biosensor or it may be a refined binding curve that is provided by manipulating one or more binding curves as will be disclosed more in detail. In one embodiment the reference binding curve is provided by acquiring, using the biosensor, one or more binding curves for a reference-analyte ligand interaction at the predetermined acquisition conditions. In some embodiments, the reference binding curve may be a theoretical binding curve that is not based directly on a binding curve acquired by a biosensor, but based on a theoretical or empirical model, e.g. a binding curve that is specifically designed to characterize a specific interaction mechanism or the like.

In the present method, the reference binding curve is representative for the reference interaction for a predetermined acquisition cycle, and the sample binding curve for the analyte ligand interaction to be evaluated is acquired using the same predetermined acquisition cycle, whereby the resulting binding curves may be evaluated by a direct comparison instead of fitting the response to a theoretical model or the like to extract specific interaction parameters for evaluation.

Throughout this disclosure, the term predetermined acquisition cycle comprises the collective steps and settings of the biosensor as well as the concentration of the analyte in the sample fluid(s), which have influence on the shape of a binding curve registered with the biosensor. According to one embodiment, the predetermined acquisition cycle comprises at least one association phase wherein the sensor surface is put into contact with a fluid sample comprising analyte at a predetermined concentration. The predetermined acquisition cycle may comprise at least one dissociation phase wherein the sensor surface is put into contact with a fluid free from analyte.

Figure 4:
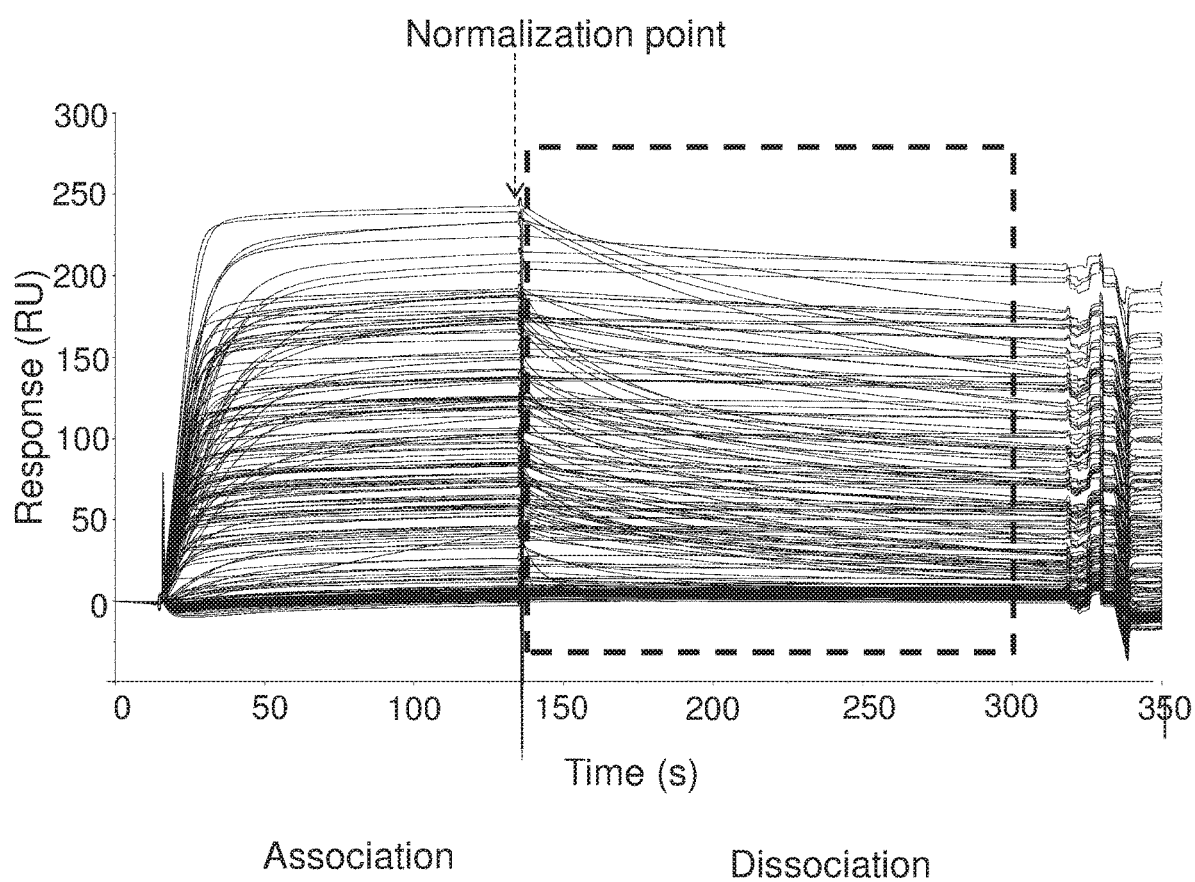
FIG. 4 shows one example of screening data obtained with analytes in a fluid sample and a ligand immobilized on a sensor surface of a biosensor in accordance with one embodiment of the present invention. In this example, antibodies were captured on a biosensor surface with immobilized anti-IgG-Fc antibody and the binding of antigen to the captured antibodies was registered.

FIG. 4 shows an example of a predetermined acquisition cycle including one association and one dissociation phase. Examples of upper and lower limit reference curves comprising one dissociation phase obtained from data in FIG. 4 is shown in FIG. 5. However, it should be noted that the predetermined acquisition cycle in no way should be limited to the example of FIG. 4, and a predetermined acquisition cycle may be designed in any suitable way to facilitate the evaluation and classification of the analyte ligand interaction. The predetermined acquisition cycle may e.g. comprise:
- one single association phase with analyte concentration $C_1$,
- several association phases at different analyte concentrations $C_1$, $C_2$ to $C_n$
- a high analyte concentration followed by a lower analyte concentration,
- cycles where an association phase is followed by a dissociation phase
- association and dissociation phases obtained with different analytes at the same or different concentrations Some parameters defined by the predetermined acquisition cycle may be related to the type of biosensor that is used and to settings of the same. For example, when the sensor surface of the biosensor is provided in a flow cell, then the predetermined acquisition cycle may also define the flow rate of fluid through the flow cell, as the association and dissociation rates under some conditions are dependent on the flow rate. Other parameters that may be relevant are the temperature at the biosensor, attenuation of ligand activity, etc.

The analyte concentrations may be prepared off line and provided in separate sample containers or the concentrations may be provided by an in line mixing unit capable of mixing a sample stock solution at high concentration with buffer or the like to a sample fluid with the predetermined concentration of analyte.

Normalization (FIG. 3, [30]) may be performed in any suitable way in accordance with the specific deviation/attenuation pattern, and according to one embodiment it may be performed by selecting a suitable point of normalization $t_N$ in the predetermined acquisition cycle and rescaling the reference-analyte ligand interaction binding curves in the y-direction so that all curves have the same value at said point $t_N$. The point of normalization is preferably selected in accordance with the predetermined acquisition cycle, and in one embodiment it is selected as a point a short time frame before the end of the association phase with highest response as indicated in FIG. 4. Another example is to select two or more points of normalization $t_N$ and to normalize the curves e.g. based on the average response at said points of normalization $t_N$.

The deviation criteria in the form of upper and lower threshold curves may be provided based on statistical information calculated from these reference binding curves. According to one embodiment, the predetermined deviation criteria for classification of the analyte ligand interaction are weighted in response to different phases or parts thereof of the predetermined acquisition cycle.

According to one embodiment, the step of classifying the analyte ligand interaction comprises the step of calculating the percentage of data points of a sample binding curve that are located outside the reference threshold curves and wherein the deviation criteria is the maximum percentage of data points allowed to be outside of the reference threshold curves.

According to one embodiment, the step of classifying the analyte ligand interaction comprises the step of calculating the sum of squares for the threshold reference binding curve and/or sample binding curve where the average reference curve have first been subtracted and wherein the classification criteria is the based on a comparison of sum of squares for different reference windows.

In one embodiment the current method comprises the step of: excluding one or more sections of the binding curves from the step of registering deviation and following steps. The exclusion of one or more sections from the binding curves may be useful to exclude regions that comprise disturbances like spikes or the like.

According to one embodiment, at least one of the ligand and analyte is selected from the group of: drug targets and natural their binding partners or reagents used to characterize drug targets.

According to one embodiment, there is provided a biosensor system arranged to perform the method according to above. The biosensor system, may e.g. be a SPR based system like the Biacore™ systems, an SPR imaging system as the MX96 system (Ibis) or e.g a waveguide interferometer like the ForteBio™ systems or the like. Still further, there is provided a computer program arranged to, when run on a computer, control the operation of a biosensor system to perform the method according above.

EXAMPLE 1

FIG. 4 shows one example of screening data obtained with analytes in a fluid sample and a ligand immobilized on a sensor surface of a biosensor in accordance with one embodiment of the present invention. In this example, antibodies were captured on a biosensor surface with immobilized anti-IgG-Fc antibody and the binding of antigen to the captured antibodies was registered.

System: Biacore T200 system was used with HBE-EP+ as running buffer and with sensor chip CM5 docked.

Immobilization: The sensor surface was activated by an injection of EDC/NHS for 7 minutes, Goat anti mouse Fcgamma antibody at 30 µg/ml in acetate buffer pH 5.0 was then injected and bound to the sensor surface. Next, the surface was deactivated with 1 M ethanolamine at pH 8.5 for 7 minutes. The immobilization procedure resulted in 13000 to 15000 RU of immobilized antibody.

Screening samples: Culture media samples suspected of containing target antibody.

Antibody capture: Screening samples were injected for 60 seconds and antibodies bound to the immobilised antibody. Capture levels ranged from 0 to 1800 with typical capture levels from 400 to 1700 RU.

Antigen injection: Antigen specific for target antibody was injected for 2 minutes with a dissociation time of 300 seconds.

Regeneration: The surface was regenerated with repeat 60 s injections of 10 mM glycine —HCl at pH 2.0 to 2.5

Data analysis: Overlay plots of antigen binding were first prepared as seen in FIG. 4. The y axis shows relative response values with binding levels up to 250 RU. The dissociation phase is identified by the black rectangle and, the arrow points to highest response during injection. This response was used for normalization of data. By normalizing the data, each sensorgram was replotted on a scale from 0 to 100, where 0 corresponds to the baseline before antigen injection and 100 to the response at the normalization point.

Figure 5A:
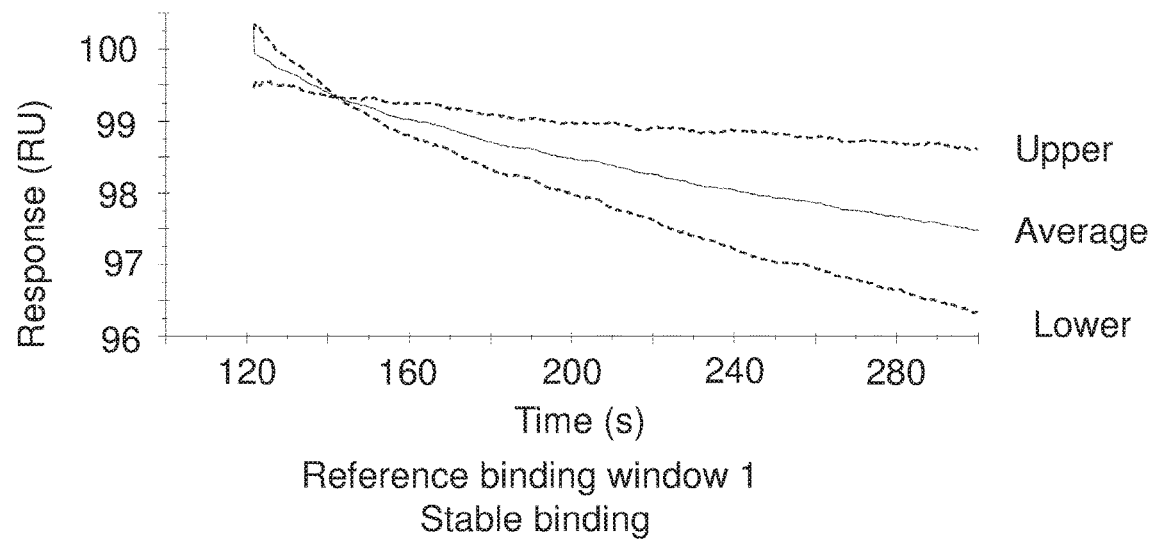
FIGS. 5a and 5b show two reference windows with normalized upper and lower binding curves characterized, in this case, by non-overlapping dissociation phases. In each reference plot the average of the limit curves is shown.
Figure 5B:
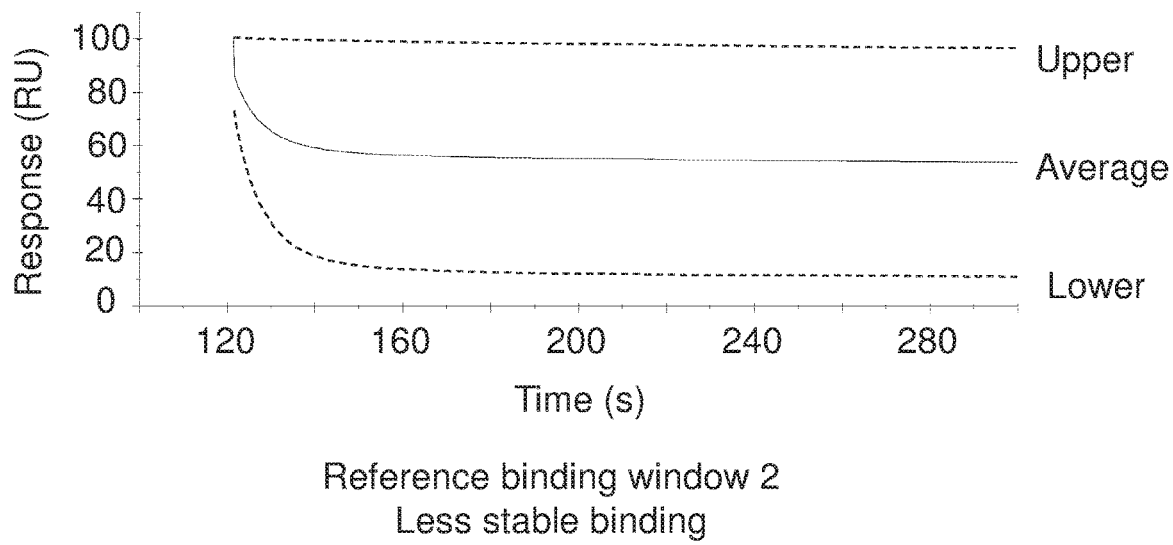

By inspection of the dissociation phases of the normalized sensorgrams two reference windows were identified as shown in FIGS. 5a and 5b. In each figure, upper and lower limit sensorgrams are shown together with the average/median sensorgram. (with only two curves the average is the same as the median). In FIG. 5a two limit sensorgrams with stable binding with more than 96% of the response remaining after 180 seconds of dissociation (dissociation starts at 120 seconds and ends at 300 s) are shown together with the average of the two curves.

In FIG. 5b curves with less stable binding are shown. The upper limit curve corresponds to a stability just below 96% and the bottom limit curve is the binding curve with the fastest dissociation observed. The middle curve is the average of these two curves. Note that for two curves the average and median values are identical (see equation below).

In the next steps of the analysis all other curves were compared with the two reference windows. If a normalized sample curve fell between the upper and lower limit curves in FIG. 5a it was sorted into the group of stable binders. If a normalized sample curve fell between the upper and lower limit curves in FIG. 5b it was sorted into the group of less stable binders. If a sample curve fell outside or partially outside the limit curves in both reference windows, the distance from each reference window was calculated in terms of a similarity score. The similarity score for each reference window was calculated using the min/max algorithm as described in Karlsson, R., Pol, E., & Frostell, Å. (2016). Comparison of surface plasmon resonance binding curves for characterization of protein interactions and analysis of screening data. Analytical biochemistry, 502, 53-63.

$$\text{Similarity score} = \%\text{ points inside limits} + \%\text{ points outside limits} * \frac{SSQ_{limit\ distance\ to\ median}}{SSQ_{sample\ distance\ to\ median}}$$

Figure 6A:
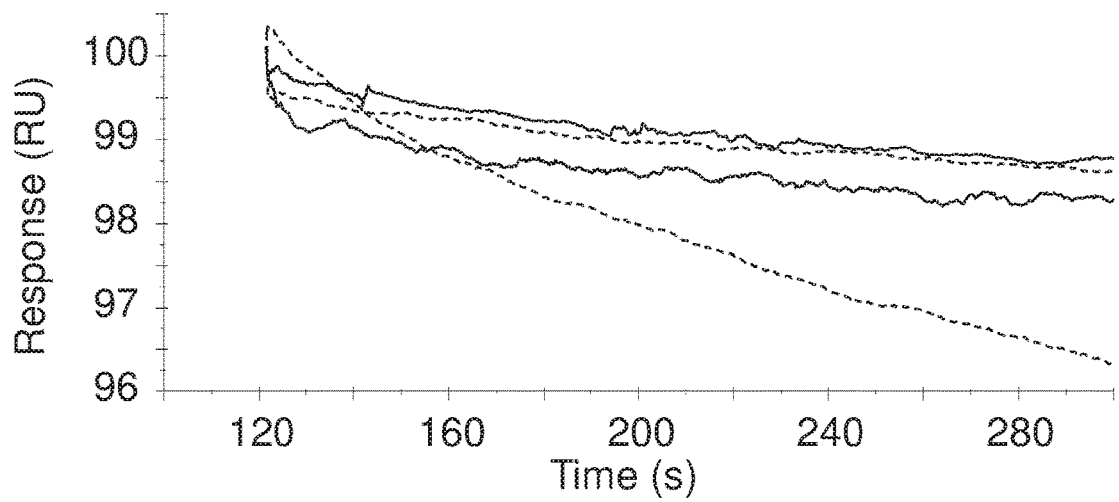
FIGS. 6a and 6b show the assignment of the sensorgram data in FIG. 4. Only two antibody/antigen interactions fit the criteria corresponding to FIG. 5a whereas all other interactions are assigned to the second reference window.
Figure 6B:
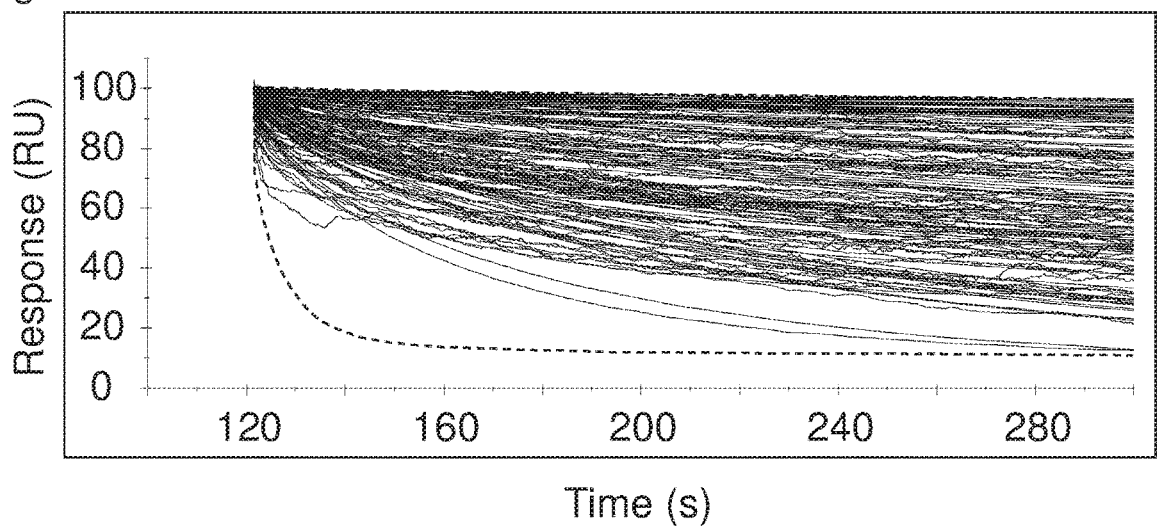

The sample curve was sorted into the reference window to which it obtained the highest similarity score. The result of this sorting procedure is shown in FIGS. 6a and 6b. Two sample curves were sorted into the stable binder group and remaining samples into the less stable binding group.

In this way, the use of two reference windows instead of one reference window made it possible to directly identify the stable binders.

When new samples are run using the same experimental procedure, with respect to antigen injection and dissociation times, the same reference windows can be reused. This will ensure consistent evaluation of new samples and makes it possible to automate the analysis as the selection of reference curves and reference windows only must be performed once.

The invention claimed is:

1. A method for screening a sample in respect of the presence of at least one specific analyte possibly present in a fluid sample by evaluating data from interaction between the specific analyte, if present, and its ligand or binding partner, which comprises the steps of:
   a) providing a biosensor defining a sensor surface comprising at least one immobilized ligand, wherein each ligand is known to bind and interact with a specific analyte;
   b) obtaining a plurality of different reference binding curves, each representing a specific binding behavior between a specific analyte of a plurality of specific analytes and its ligand, or binding partner known to interact with the specific analyte of the plurality of specific analytes, for a predetermined acquisition cycle;
   c) acquiring, using the biosensor, a sample binding curve for interaction between the specific analyte possibly present in the fluid sample and its ligand or binding partner for the same predetermined acquisition cycle;
   d) registering the deviation of the sample binding curve from the reference binding curves to form at least two reference interaction windows including a stable binding reference interaction window associated with more than 96% of sensor response remaining after 180 seconds of dissociation and a less stable binding reference interaction window associated with less than 96% of sensor response remaining after 180 seconds of dissociation;
   e) assigning the interaction between the specific analyte and its ligand or binding partner from step c) to reference interaction window of the at least two reference interaction windows to which it shows the smallest registered deviation; and
   f) optionally repeating steps c)-e) with additional fluid samples.

2. The method according to claim 1, wherein 1-1000 ligands are immobilized as discrete areas or spots on said sensor surface.

3. The method according to claim 1, wherein the sample binding curve is obtained between the specific analyte and the immobilized ligand or between the specific analyte and its binding partner when the specific analyte is bound to the immobilized ligand.

4. The method according to claim 1, wherein the ligand and specific analyte is selected from antibodies, fragments thereof or other binding molecules; and the binding partner is selected from antigen or other target molecules.

5. The method according to claim 1, wherein at least one of the ligand, binding partner and analyte is selected from the group of: drug targets and their binders or reagents used to characterize drug targets, such as receptors, cytokines, antibodies, peptides, apatamers and low molecular weight compounds, for example from compound libraries.

6. The method according to claim 1, comprising the step of normalizing sample binding curves that are at zero baseline with respect to the highest response obtained in each sample binding curve before step d).

7. The method according to claim 6, wherein normalization is based on the binding curve value at a point in the predetermined acquisition cycle just before the end of an association phase.

8. The method according to claim 6, wherein normalization is based on a freely selectable point in the predetermined acquisition cycle.

9. The method according to claim 1, wherein the biosensor is an SPR biosensor and the binding behaviors between ligand and analyte comprise association and dissociation, for example slow association-slow dissociation, slow association-fast dissociation, fast association-slow dissociation, fast association-fast dissociation, wherein the association- dissociation combinations could be mono- or biphasic.

10. The method according to claim 1, comprising the step of providing an upper and/or a lower reference threshold curve in each reference interaction window, whereby each specific window represents a range of analyte behavior.

11. The method according to claim 1, wherein the reference binding curves are provided either by using the biosensor or by computer simulation.

12. The method according to claim 1, wherein the predetermined acquisition cycle comprises at least two consecutive association phases for different analyte concentrations.

13. The method according to claim 1, wherein the sensor surface of the biosensor is provided in a flow cell and wherein the predetermined acquisition cycle defines the flow rate of fluid through the flow cell.

14. The method according to claim 1, comprising the step of:
   excluding one or more sections of the binding curves from the step of registering deviation and following steps.

15. The method according to claim 14, wherein excluded sections comprise transitions between association and dissociation phases as defined by the predetermined acquisition cycle.

16. The method according to claim 1, comprising the step of:
   displaying on a graphical display, for visual inspection-a plot of the reference binding windows, where assigned samples are displayed in an overlay plot together with the upper and lower reference curves.

17. The method according to claim 1, comprising the step of calculating the percentage of data points of a sample binding curve that are located outside the reference threshold curves and wherein the deviation criteria is the maximum percentage of data points allowed to be outside of the reference threshold curves.

18. The method according to claim 1, comprising the step of calculating the sum of squares for threshold reference binding curve or sample binding curve where the reference curve has first been subtracted and using the ratio of the sum of squares as an evaluation criteria for registering the deviation of the sample binding curve from the reference binding curves.

19. The method according to claim 1, wherein a predetermined deviation criteria for registering the deviation of the sample binding curve from the reference binding curves is weighted in response to different phases of the predetermined acquisition cycle.

\* \* \* \* \*